US007264948B2

(12) United States Patent
Robbins et al.

(10) Patent No.: US 7,264,948 B2
(45) Date of Patent: Sep. 4, 2007

(54) POLYPEPTIDES FOR INCREASING MUTANT CFTR CHANNEL ACTIVITY

(75) Inventors: Paul D Robbins, Mt. Lebanon, PA (US); Raymond Frizzell, Pittsburgh, PA (US); Zhibao Mi, Pittsburgh, PA (US); Fei Sun, Warrendale, PA (US)

(73) Assignee: University of Pittsburgh, Pittsburgh, PA (US)

( * ) Notice: Subject to any disclaimer, the term of this patent is extended or adjusted under 35 U.S.C. 154(b) by 319 days.

(21) Appl. No.: 10/650,435

(22) Filed: Aug. 28, 2003

(65) Prior Publication Data

US 2004/0115770 A1    Jun. 17, 2004

Related U.S. Application Data

(60) Provisional application No. 60/407,461, filed on Aug. 30, 2002.

(51) Int. Cl.
C07K 14/435 (2006.01)
C07K 14/47 (2006.01)
A61K 38/00 (2006.01)

(52) U.S. Cl. ............... 435/69.1; 435/252.3; 435/320.1; 435/455; 530/350; 530/325

(58) Field of Classification Search ................ 530/350, 530/325; 435/69.1, 252.3, 320.1
See application file for complete search history.

(56) References Cited

U.S. PATENT DOCUMENTS 4,980,286 A   12/1990 Morgan et al. ............. 435/371
6,881,825 B1 * 4/2005 Robbins et al. ............. 530/327
2003/0104622 A1  6/2003 Robbins et al.
2003/0219826 A1 11/2003 Robbins et al.

OTHER PUBLICATIONS

Meacham et al. [The EMBO Journal, 18(6): 1492-1505 (1999).*
Egan et al., 2002, "Calcium-pump inhibitors induce functional surface expression of ΔF508-CFTR protein in cystic fibrosis epithelial cells", *Nature Medicine* 8: 485-492.
Shwarze et al., 1999, "In Vivo Protein Transduction: Delivery of a Biologically Active Protein into the Mouse", *Science* 285:1569-72.
Vocero-Akbani et al., 1999, "Killing HIV-infected cells by transduction with an HIV protease-activated caspase-3 protein", *Nat. Med.* 5:29-33.
Sheppard, DN et al., 1999, "Structure and Function of the CFTR Chloride Channel", *Physiol. Rev* 79:S23-45.
Elliot et al., 1999, "Intercellular trafficking of VP22-GFP fusion proteins", *Gene Therapy* 6:149-51.
Nagahara et al., 1998, "Transduction of full-length TAT fusion proteins into mammalian cells: TAT-p27[Kip1] induces cell migration", *Nat. Med.* 4:1449-52.
Derossi et al., 1998, "Trojan peptides: the penetratin system for intracellular delivery", *Trends in Cell Biology* 8:84-87.

Villaverde et al., 1998, "A cell adhesion peptide from foot-and-mouth disease virus can direct cell targeted delivery of a functional enzyme", *Biotechnology and Bioengineering* 59:294-301.
Vives et al., "A Truncated HIV-1 Tat Protein Basic Domain Rapidly Translocates through the Plasma Membrane and Accumulates in the Cell Nucleus", *J. Biol. Chem.* 272:16010-17 (1997).
Elliot & O'Hare, 1997, "Intercellular Trafficking and protein Delivery by a Herpesvirus Structural Protein", *Cell* 188:223-233.
Moy et al., 1996, "Tat-Mediated Protein Delivery Can Facilitate MHC Class I Presentation of Antigens", *Mol. Biotechnol.* 6:105-13.
Howard et al., 1995, "Epitope tagging permits cell surface detection of functional CFTR", *Am J. Physiol.* 269:C1565-76.
Fawell et al., 1994, "Tat-mediated delivery of heterologous proteins into cells", *Proc. Natl. Acad. Sci. USA* 91:664-668.
Hollenberg et al., 1994, "Multiple promoter elements in the human chorionic gonadotropin β subunit genes distinguish their expression from the luteinizing hormone β gene", *Mol. Cell. Endocrinology* 106:111-119.
Goldspiel et al., 1993, "Human gene therapy", *Clinical Pharmacy* 12:488-505.
Tolstoshev, 1993, "Gene therapy, concepts, current trials and future directions", *Ann. Rev. Pharmacol. Toxicol.* 33:573-596.
Mulligan, 1993, "The Basic Science of Gene Therapy", *Science* 260:926-932.
Morgan and Anderson, 1993, "Human Gene Therapy", *Annu. Rev. Biochem.* 62:191-217.
1993, TIBTECH 11(5):155-215.
Miller et al., 1993, "Use of Retroviral Vectors for Gene Transfer and Expression", *Meth. Enzymol.* 217:581-599.
Kozarsky and Wilson, 1993, "Gene therapy: advenovirus vectors", *Current Opinion in Genetics and Development* 3:499-503.

(Continued)

Primary Examiner—Tekchand Saidha
(74) Attorney, Agent, or Firm—Baker Botts LLP

(57) ABSTRACT

The present invention provides methods and compositions for enhancing channel activity to the mutant cystic fibrosis trans-membrane conductance regulator protein (CFTR). The compositions of the invention comprise polypeptides containing CFTR sub-domains that are designed to mimic the folding defect of the full length mutant CFTR proteins, resulting in competitive binding to cytoplasmic chaperones such as Hsc/Hsp70 and Hdj2. The methods of the invention comprise transduction, or recombinant expression, of CFTR polypeptides in a cell expressing mutant CFTR. The presence of the CFTR polypeptide results in a dominant effect whereby the CFTR polypeptide competes with the endogenously expressed mutant CFTR for binding to cytoplasmic chaperones such as Hsc/Hsp70 and Hdj2. Mutant CFTR proteins include, but are not limited to, ΔF508 CFTR. The present invention is based on the discovery that reduced binding of cytoplasmic chaperones to the endogenous ΔF508 CFTR, mediated by the presence of CFTR polypeptides, results in restoration of plasma membrane localization and channel activity. The methods and compositions of the invention can be used to restore channel activity in cystic fibrosis subjects carrying genetic defects in the CFTR gene, such as for example, ΔF508 CFTR.

5 Claims, 10 Drawing Sheets

OTHER PUBLICATIONS

Wu and Wu, 1991, "Delivery systems for gene therapy", *Biotherapy* 3:87-95.

Green & Lowenstein, 1988, "Autonomous Functional Domains of Chemically Synthesized Human Immunodeficiency Virus Tat Trans-Activator Protein", *Cell*, 55:1179-1188.

Frankel & Pabo, 1988, "Cellular Uptake of the Tat Protein from Human Immunodeficiency Virus", *Cell* 55:1189-1193.

Wu and Wu, 1987, "Receptor-mediated in Vitro Gene Transformation by a Soluble DNA Carrier System", *J. Biol. Chem.* 262:4429-4432.

Brinster et al., 1982, "Regulation of metallothionein-thymidine kinase fusion plasmids injected into mouse eggs", *Nature* 296:39-42.

Benoist, C. and Chambon, P. 1981, "In vivo sequence requirements of the SV40 early promoter region", *Nature* 290:304-310.

Wagner et al., 1981, "Nucleotide sequence of the thymidine kinase gene of herpes simplex virus type1", *Proc. Natl. Acad. Sci. U.S.A.* 78:1441-1445.

Yamamoto et al., 1980, "Identification of a Functional Promoter in the Long Terminal Repeat of Rous Sardoma Virus", *Cell* 22:787-797.

* cited by examiner

A.

B.

C.

A.

B.

US 7,264,948 B2

POLYPEPTIDES FOR INCREASING MUTANT CFTR CHANNEL ACTIVITY

PRIORITY CLAIM

This application claims priority to U.S. Provisional Application No. 60/407,461 filed Aug. 30, 2002.

This invention is made in part with support from the National Institute of Health under grant number DK56490.

1. INTRODUCTION

The present invention provides methods and compositions for enhancing channel activity to cells expressing the mutant cystic fibrosis trans-membrane conductance regulator protein (CFTR). The compositions of the invention comprise polypeptides containing CFTR sub-domains that are designed to mimic the folding defect of the full length mutant CFTR proteins, resulting in competitive binding to cytoplasmic chaperones such as Hsc/Hsp70 and Hdj2. The methods of the invention comprise transduction, or recombinant expression, of CFTR polypeptides in a cell expressing mutant CFTR. The presence of the CFTR polypeptide results in a dominant effect whereby the CFTR polypeptide competes with the endogenously expressed mutant CFTR for binding to cytoplasmic chaperones such as Hsc/Hsp70 and Hdj2. Such mutant CFTR proteins include, but are not limited to, ΔF508 CFTR. The present invention is based on the discovery that reduced binding of cytoplasmic chaperones to the endogenous ΔF508 CFTR, mediated by the presence of CFTR polypeptides, results in restoration of plasma membrane localization and channel activity. The methods and compositions of the invention can be used to restore channel activity in cystic fibrosis subjects carrying genetic defects in the CFTR gene, such as for example, ΔF508 CFTR.

2. BACKGROUND OF THE INVENTION

Cystic fibrosis is a lethal genetic disease afflicting approximately 30,000 individuals in the United States. Approximately 1 in 2500 Caucasians is born with the disease, making it the most common lethal, recessively inherited disease in that population.

Cystic fibrosis affects the secretory epithelia of a variety of tissues, altering the transport of water and salt into and out of the blood stream. In particular, the ability of epithelial cells in the airways, pancreas and other tissues to transport chloride ions, and accompanying sodium and water, is severely reduced in cystic fibrosis patients, resulting in respiratory, pancreatic and intestinal ailments. The clinical manifestation of cystic fibrosis is respiratory disease, characterized by airway obstruction due to the presence of a thick mucus that is difficult to clear from airway surfaces. This thickened airway liquid results in recurrent bacterial infections and progressively impaired respiration, eventually leading to death.

Cystic fibrosis is caused by mutations in the gene encoding the cystic fibrosis transmembrane conductance regulator (CFTR). The coding regions of CFTR are composed of 27 exons dispersed over 250,000 base pairs (250Kb) of genomic DNA. During transcription, introns are spliced out and exons are joined together to form a 6100-bp mRNA transcript that is translated into the 1480 amino acid sequence of CFTR protein The normal CFTR protein is a chloride channel protein found in membranes of cells that line the passageways of the lung, pancreas, colon and genitourinary tract. The CFTR protein is made up of five domains: two membrane-spanning domains (MSD1 and MSD2) that form the chloride ion channel, two nucleotide-binding domains (NBD1 and NBD2) that bind and hydrolyze adenosine triphosphate (ATP), and a regulatory (R) domain.

Protein synthesis normally involves interactions between amino acid side chains that results in folding of the protein into a thermodynamically preferred three dimensional structure. Proper protein localization within the cell is dependent on the protein forming the correct conformation. Some proteins appear to require interaction with other molecules in order to fold properly. Such molecules include proteins referred to as "molecular chaperones." Chaperones stabilize newly synthesized polypeptides until they are assembled into their proper native structure.

The most common cause of cystic fibrosis which accounts for 70% of all cystic fibrosis cases results from a three nucleotide deletion that results in deletion of phenylalanine residue 508 (ΔF508 CFTR). The ΔF508 mutation occurs in the nucleotide sequence that codes for the first nucleotide-binding domain (NBD1) and results in retention of the mutant protein in the endoplasmic reticulum (ER) and subsequent degradation by the ubiquitin-proteosome pathway. The mechanism responsible for ER retention of the ΔF508 CFTR protein includes associations with cytoplasmic chaperones such as Hsc/Hsp70 and Hdj2.

One recently developed approach for the transfer of various cargo to cells involves the use of novel cell-targeting ligands, which increase the rate and specificity for the transport of molecules. Such ligands are also known as protein transduction domains (PTDs). The first protein discovered having such transduction properties was the HIV transactivator protein, TAT. See Green & Lowenstein, *Cell*, 55:1179-1188 (1988); Frankel & Pabo, *Cell* 55:1189-1193 (1988). Subsequently, an 11 amino acid transduction domain in TAT (TAT-PTD) responsible for the observed transduction properties was identified, based on its high basic residue content. See Fawell et al., *Proc. Natl. Acad. Sci. USA* 91:664-668 (1994). It has been shown that fusion protein constructs containing TAT-PTD are capable of delivering proteins to a wide spectrum of cell types both in vitro and in vivo. See Nagahara et al., *Nat. Med.* 4:1449-52 (1998); Vives et al., *J. Biol. Chem.* 272:16010-17 (1997); Shwarze et al., *Science* 285:1569-72 (1999); Vocero-Akbani et al., *Nat. Med.* 5:29-33 (1999); Moy et al., *Mol. Biotechnol.* 6:105-13 (1996). Other peptides having translocating properties include, for example, penetratins (Derossi et al., 1998, *Trends in Cell Biology* 8:84-87), Drosophila Antennapedia homeodomain, the cell attachment motif of foot and mouth disease virus (FMDV) (Villaverde et al., 1998, *Biotechnology and Bioengineering* 59:294-301); and VP-22 (Elliot & O'Hare, *Cell* 188:223-233 (1997)).

PTDs can be used to deliver full length proteins as well as small peptides. The advantage to protein transduction appears to be the efficiency of delivery and may be used to deliver cargo to treat various acute diseases, as well as chronic diseases, both genetic and acquired.

The efficiency of PTDs is apparently linked to its mechanism of action. PTDs interact electrostatically with anionic elements, such as GAGs, on the cell surface. These contacts draw the PTDs in close proximity to the plasma membrane where, by one or more unknown mechanisms, including, in all likelihood, endocytosis where the PTDs and their cargoes are delivered into the cell. Thus, because of the electrostatic interactions, the length and degree of charge within the PTDs can modify its efficiency. Therefore, longer peptides (10 and 12 mers) are better able to mediate transduction in GAG-deficient lines than short PTDs, although short PTDs (4 and 6-mers) still possess an intrinsic capacity for protein transduction, provided they can bind to the cell surface via interactions with charged dextran polymers.

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, but their long-term beneficial effects have not been established and such therapies are not presently available to patients.

Accordingly, improvements are needed in the treatment of cystic fibrosis. The present invention fulfills this need and further provides other related advantages.

3. SUMMARY OF THE INVENTION

The present invention provides compositions and methods for enhancing chloride transport in epithelial cells expressing mutant forms of the CFTR protein. Specifically, the invention provides methods and compositions for transduction or expression of CFTR polypeptides comprising sub-domains of the CFTR protein designed to mimic the folding defect of the full length mutant CFTR protein in an epithelial target cell.

Specifically, the compositions of the invention include CFTR polypeptides comprising sub-domains which are designed to compete with the endogenously expressed mutant CFTR, such as ΔF508, for binding to molecular chaperones such as Hsc/Hsp70 and Hdj2. In a preferred embodiment of the invention, the CFTR polypeptides may comprise the ΔF508 CFTR mutation thereby providing a more structurally related peptide mimic. In yet another embodiment of the invention the CFTR polypeptides of the invention are linked to an internalizing peptide, also referred to as a protein transduction domain, that facilitates the delivery and uptake of polypeptides into a target cell. The present invention also provides nucleic acid molecules encoding CFTR polypeptides capable of restoring CFTR mediated chloride channel activity.

While not wishing to be bound by any one particular theory, it is believed that prolonged binding of molecular chaperones to the endogenously expressed mutant CFTR results in retention in the endoplasmic reticulum (ER) of the cell, thereby leading to protein degradation. The CFTR polypeptides of the invention are believed to compete with the endogenously expressed mutant CFTR for binding to molecular chaperones, thereby decreasing retention of the mutant CFTR in the endoplasmic reticulum (ER) and diminishing protein degradation by the ubiquitin-proteosome pathway.

The methods of the present invention encompass contacting the CFTR polypeptides, or nucleic acid molecules capable of encoding such polypeptides, with a target epithelial cell that express an endogenous mutant CFTR. The CFTR polypeptides are designed to compete with endogenous mutant CFTR for molecular chaperone binding, thereby reducing degradation of endogenous mutant CFTR. The compositions and methods of the invention may be used to alleviate the symptoms associated with loss of CFTR function resulting in cystic fibrosis.

4. BRIEF DESCRIPTION OF THE DRAWINGS

FIG. 1 shows light micrographs of various cell lines stained with X-gal, demonstrating PTD-5-facilitated protein transduction. (A) HIG-82 cells; (B) rabbit primary synovial cells; (C) human primary synovial cells; (D) primary human airway epithelial cells (HBE144); (E) polarized canine kidney cells (MDCK), (F) human islets; (G) murine myoblasts (C2C12); (H) murine fibrosarcoma tumor line (MCA205); (I) NIH3T3 cells.

5. DETAILED DESCRIPTION OF THE INVENTION

Figure 1:
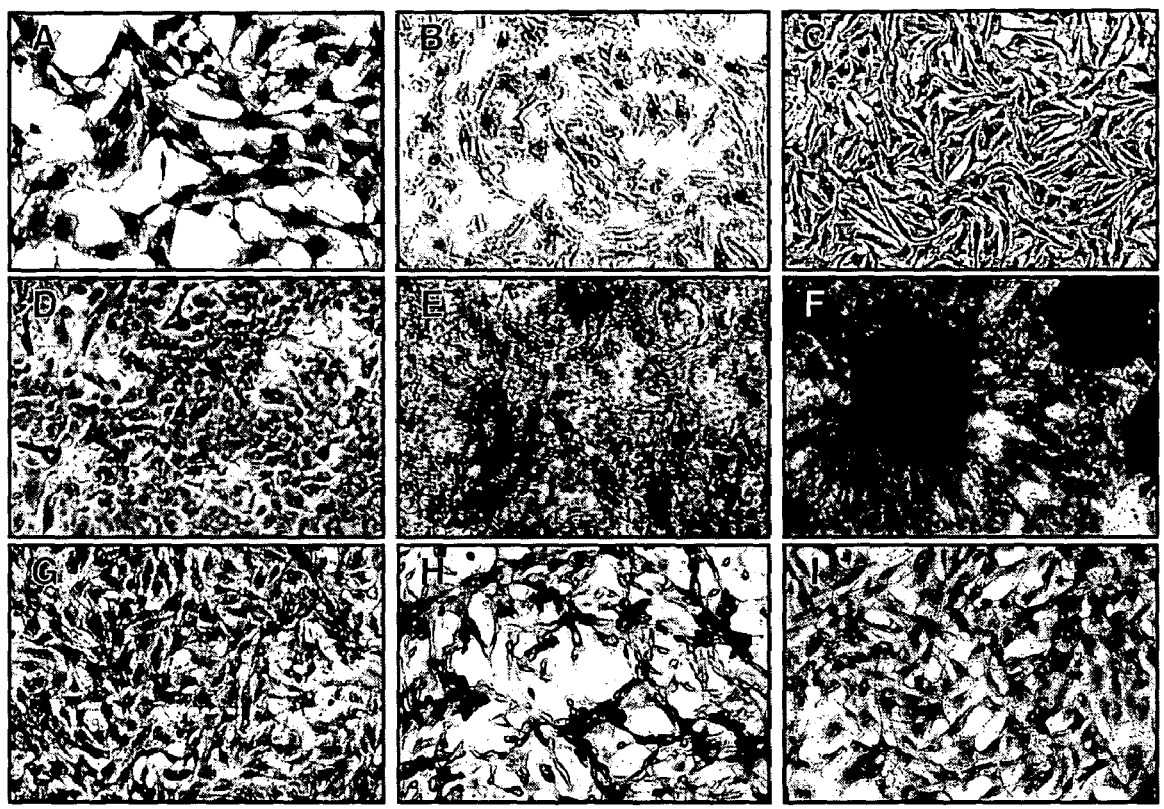

The present invention provides methods and compositions for increasing chloride channel activity in epithelial cells expressing mutant CFTR. Such mutants include, but are not limited to the ΔF508 CFTR mutant. The compositions of the invention include CFTR polypeptides, or nucleic acids capable of expressing such CFTR polypeptides, capable of competitive binding to molecular chaperones normally associated with CFTR and nucleic acid molecules encoding such CFTR polypeptides. The methods of the invention include delivery of the CFTR polypeptides, or expression of nucleic acid molecules encoding such polypeptides, in epithelial cells expressing mutant CFTR.

In yet another embodiment of the invention, compounds or agents capable of inhibiting molecular chaperone activity, or expression, may be used to enhance channel activity in cells expressing mutant CFTR. Such agents include, for example, agents that bind chaperones and thereby inhibit interaction with the CFTR protein. Additionally, chaperone anti-sense, ribozymes and/or RNAi molecules may be utilized to inhibit chaperone expression in a cell.

In another embodiment of the invention, compounds capable of inhibiting molecular chaperone activity may be used to promote or enhance the activity of a mutant protein when the mutation results in a trafficking defect due to association of the mutant protein with molecular chaperones. Examples of such proteins may include those known to be related to trafficking or processing defects in genes associated with various disorders, such as Alzheimer's disease, Parkinson's disease, ALS (amylotrophic lateral sclerosis), Huntington's disease, prion-related disorders, etc.

The methods and compositions of the invention may be used to enhance chloride channel activity in epithelial cells expressing the mutant CFTR protein. In particular, the methods and compositions of the invention may be used to enhance chloride channel activity in subjects suffering from the genetic disease cystic fibrosis.

5.1 Structure of CFTR Polypeptides

The present invention provides compositions for restoring chloride channel activity in epithelial cells expressing mutant CFTR. The compositions of the invention include polypeptides comprising CFTR sub-domains. As used herein, "CFTR polypeptides" include those comprising CFTR subdomains as well as those linked to internalizing peptides. Preferred subdomains include those capable of binding to chaperones. In an embodiment of the invention, the preferred subdomains include, for example, sequences residing in the NBD1 and R domains. In a preferred embodiment of the invention, the CFTR polypeptides comprise subdomains having the ΔF508 mutation. In yet another embodiment of the invention, the CFTR polypeptide is associated with an internalizing peptide which functions to facilitate delivery and uptake of polypeptides into the epithelial cells expressing mutant CFTR. The polypeptides of the invention are designed to compete with endogenously expressed mutant CFTR for binding to molecular chaperones thereby reducing the degradation of the endogenously expressed mutant CFTR.

The CFTR protein is comprised of five functional domains which include two membrane spanning domains (MSD1 and MSD2) that form the chloride ion channel, two nucleotide-binding domains (NBD1 and NBD2) that bind and hydrolyze adenosine triphosphate (ATP), and a regulatory (R) domain. The nucleotide and amino acid sequence of the ΔF508 protein, as well as the boundaries of the different domains is known (Sheppard, DN et al., 1999, Physiol. Rev 79:S23-45). The ΔF508 mutation is located in the first nucleotide-binding domain.

The CFTR polypeptides of the invention include those polypeptides comprising subdomains of the CFTR protein capable of association with molecular chaperones and restoration of CFTR channel activity. In a specific embodiment of the invention CFTR subdomains corresponding to sequences located within the nucleotide-binding domain (NBD) and regulatory (R) domain are included in the CFTR polypeptide of the invention. In a specific embodiment of the invention, a NBD-RD CFTR peptide comprises 397 amino acids from amino acid residue 444 to 841. In yet another embodiment of the invention, the NBD1-RD polypeptide comprises a deletion of amino acid residue 508.

Additionally, identification of CFTR polypeptides capable of binding to molecular chaperones may be accomplished using a variety of methods. For example, in vitro binding assays may be performed wherein recombinantly expressed molecular chaperones such as Hdj2 or Hsc/Hsp70 are contacted with a recombinantly expressed test CFTR polypeptide for a sufficient time to permit interaction between the chaperone and the CFTR polypeptide. An observed interaction between the molecular chaperone and the CFTR polypeptide indicates the identification of a polypeptide potentially capable of increasing channel activity in epithelial cells expressing mutant CFTR.

Alternatively, in vivo assays may be performed wherein a test CFTR polypeptide is expressed in a cell expressing molecular chaperones. Test CFTR polypeptides may then be isolated from the cell and analyzed to determine whether the test CFTR polypeptide associates with molecular chaperones. A variety of different assays known to those of skill in the art may be used to detect the association of the test CFTR polypeptide with molecular chaperones. Such assays include, for example, immunoassays such as immunoprecipitations and Western blots. In addition an interaction trap/two hybrid system may be utilized to detect interactions between proteins (see, Coligan et al., Current Protocols in Protein Science, 1995-2002, John Wiley & Sons, Inc.).

Once a CFTR polypeptide capable of association with a molecular chaperone has been identified, the polypeptide is tested for its ability to enhance chloride channel activity in epithelial cells expressing endogenous mutant CFTR protein. Such assays may be performed by, for example, recombinant expression of the test CFTR polypeptide in epithelial cells expressing an endogenous mutant CFTR protein, followed by measurement of chloride channel activity. Chloride channel activity can be measured using, for example, SPQ (Howard et al., 1995, Am J. Physiol 269:C1565-76) and patch clamp methods.

In a specific embodiment of the invention CFTR polypeptides fused to a internalizing polypeptide may also be produced and tested for binding to molecular chaperones and restoration of chloride channel activity. As used herein, a transduction polypeptide is any polypeptide that enhances delivery of a polypeptide into a target cell. Such transduction polypeptides are described in U.S. patent application Ser. Nos. 10/075,869 and 10/366,493, the disclosures of which are incorporated by reference in their entirety herein.

In yet another embodiment of the invention, the CFTR polypeptides of the invention, including those with or without an internalizing peptide sequence, may further comprise a secretion leader sequence that directs secretion of polypeptides across the cell membrane. Following recombinant expression and secretion of such CFTR polypeptides, the secreted CFTR polypeptides may transduce neighboring cells and/or enter the bloodstream where cells at a distance can be transduced thereby restoring CFTR channel activity to the transduced cells.

5.2. Production of CFTR Polypeptides

The CFTR polypeptides of the invention, including those linked to a internalizing peptide and/or a secretion leader sequence, can be synthesized using a variety of different methods. Such methods include solid-phase peptide synthesis (spps) as described in Coligan et al. (Current Protocols in Protein Science, 1995-2002, John Wiley & Sons, Inc.). In addition, cloning techniques known in the art may be used for cloning of a nucleic acid molecule encoding the CFTR polypeptide of interest into an expression vector. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

As used herein, "internalizing peptide" or "protein transduction domain" (PTD) is a peptide that has been selected for its ability to locate and enter a wide variety of cell types. The PTDs are positively charged and amphipathic and may interact with negative charges on the surface of the cellular bilayer membrane. Internalizing peptides may also be designed to translocate into the nucleus of the cell. Furthermore, the internalizing peptides may be used for the translocation and delivery of cargo, such as but not limited to the CFTR polypeptides of the invention, into a cell when linked to the cargo.

The PTDs may be modified for the improvement of uptake and stability of the peptides by the addition of agents, such anionic polymers including dextran sulfate, heparin sulfate, and protamine sulfate into the cellular environment or by modification of peptides.

Nucleic acid molecules encoding the CFTR polypeptides of the invention may be recombinantly engineered into a variety of host vector systems that also provide for replication of the DNA in large scale and contain the necessary elements for directing the transcription of the CFTR polypeptide. The use of such a construct to transfect target epithelial cells of a cystic fibrosis subject will result in the transcription of sufficient amounts of the CFTR polypeptide and thereby restore CFTR channel activity. For example, a vector can be introduced in vivo such that it is taken up by a cell and directs the transcription of the CFTR polypeptide. Such a vector can remain episomal or become chromosomally integrated, as long as it can be transcribed to produce the desired CFTR polypeptide. Such vectors can be constructed by recombinant DNA technology methods standard in the art.

Vectors encoding the CFTR polypeptide of interest can be plasmid, viral, or others known in the art, which are used for replication and expression in mammalian cells. Expression of the sequence encoding the CFTR polypeptide can be regulated by any promoter/enhancer sequences known in the art to act in mammalian, preferably human cells. Such promoters/enhancers can be inducible or constitutive. Such promoters include but are not limited to: the SV40 early promoter region (Benoist, C. and Chambon, P. 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the viral CMV promoter, the human chorionic gonadotropin-β promoter (Hollenberg et al., 1994, Mol. Cell. Endocrinology 106:111-119), etc. In a preferred embodiment of the invention, an epithelial cell specific promoter/enhancer sequence may be used to promote the synthesis of CFTR in epithelial cells. Such promoters include, for example, the endogenous CFTR promoter.

Vectors for use in the practice of the invention include any eukaryotic expression vectors, including but not limited to viral expression vectors such as those derived from the class of retroviruses, adenoviruses or adeno-associated viruses.

5.3. Uses of the CFTR Polypeptide

The compositions and methods of the present invention can be utilized to restore chloride channel activity in cells expressing mutant CFTR, such as epithelial cells of cystic fibrosis patients. Specifically, delivery of CFTR polypeptides can be used to increase the level of endogenous CFTR-mediated chloride channel activity. The CFTR polypeptides of the invention are designed to compete with endogenously expressed mutant CFTR for binding to molecular chaperones thereby increasing chloride channel activity of ΔF508 CFTR.

Various delivery systems are known and can be used to transfer the compositions of the invention into cells, e.g., encapsulation in liposomes, microparticles, microcapsules, recombinant cells capable of expressing the composition, receptor-mediated endocytosis (see, e.g., Wu and Wu, 1987, J. Biol. Chem. 262:4429-4432), construction of a nucleic acid as part of a retroviral, adenoviral, adeno-associated viral or other vector, injection of DNA, electroporation, calcium phosphate mediated transfection, etc.

In a preferred embodiment of the invention, the CFTR polypeptides are administered as a fusion peptide comprising an internalizing polypeptide. Such polypeptides are capable of facilitating the delivery and uptake of polypeptides into a target cell. The internalizing polypeptides may be linked to CFTR polypeptide using a variety of different methods. As used herein, the term "link" refers to any covalent cross-linkage or non-covalent linkage wherein said linkage is between the transducing polypeptide and the CFTR polypeptide. Such methods include but are not limited to chemical cross-linking, enzymatic proteinligation, avidin bridge or glutathione-S-transferase bridge formation. Alternatively, the transducing peptide and the CFTR polypeptide may be recombinantly expressed as a fusion protein. Internalizing peptides to be used in conjunction with CFTR polypeptides, include for example, those depicted in Table I (See, Example 7).

The compositions and methods can be used to provide sequences encoding a CFTR polypeptide to cells of an individual with an inherited genetic disorder wherein expression of the CFTR polypeptide produces a normal phenotype, i.e., a functional chloride channel.

In a preferred embodiment, nucleic acids comprising a sequence encoding a CFTR polypeptide are administered to promote CFTR channel function, by way of gene delivery and expression into a host cell. In this embodiment of the invention, the nucleic acid mediates an effect by promoting CFTR production. Any of the methods for gene delivery into a host cell available in the art can be used according to the present invention. For general reviews of the methods of gene delivery see Strauss, M. and Barranger, J. A., 1997, *Concepts in Gene Therapy*, by Walter de Gruyter & Co., Berlin; Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 33:573-596; Mulligan, 1993, *Science* 260:926-932; and Morgan and Anderson, 1993, *Ann. Rev. Biochem.* 62:191-217; 1993, TIBTECH 11(5):155-215. Exemplary methods are described below.

Delivery of the CFTR polypeptide into a host cell may be either direct, in which case the host is directly exposed to the CFTR polypeptide or CFTR polypeptide encoding nucleic acid molecule, or indirect, in which case, host cells are first transformed with the CFTR polypeptide or CFTR polypeptide encoding nucleic acid molecule in vitro, then transplanted into the host. These two approaches are known, respectively, as in vivo or ex vivo gene delivery.

In a specific embodiment, the nucleic acid is directly administered in vivo, where it is expressed to produce the CFTR polypeptide. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont, Bio-Rad), or coating with lipids or cell-surface receptors or transfecting agents, encapsulation in liposomes, microparticles, or microcapsules, or by administering it in linkage to a peptide which is known to enter the cell, by administering it in linkage to a ligand subject to receptor-mediated endocytosis (see e.g., Wu and Wu, 1987, *J Biol. Chem.* 262:4429-4432).

In a specific embodiment, a viral vector that contains CFTR polypeptide encoding nucleic acids can be used. For example, a retroviral vector can be utilized that has been modified to delete retroviral sequences that are not necessary for packaging of the viral genome and integration into host cell DNA (see Miller et al., 1993, *Meth. EnzymoL* 217:581-599). Alternatively, adenoviral or adeno-associated viral vectors can be used for gene delivery to cells or tissues. (See, Kozarsky and Wilson, 1993, *Current Opinion in Genetics and Development* 3:499-503 for a review of adenovirus-based gene delivery).

In a preferred embodiment of the invention an adenovirus or adeno-associated viral vector may be used to deliver nucleic acid molecules capable of encoding the CFTR polypeptide. The vector is designed so that, depending on the level of expression desired, the promoter and/or enhancer element of choice may be inserted into the vector.

Another approach to gene delivery into a cell involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. The resulting recombinant cells can be delivered to a host by various methods known in the art. In a preferred embodiment, the cell used for gene delivery is autologous to the host cell.

In a specific embodiment of the invention, epithelial cells may be removed from a subject having cystic fibrosis and transfected with a nucleic acid molecule capable of encoding a CFTR polypeptide designed to correct a CFTR genetic disorder. Cells may be further selected, using routine methods known to those of skill in the art, for integration of the nucleic acid molecule into the genome thereby providing a stable cell line expressing the CFTR polypeptide of interest. Such cells are then transplanted into the subject thereby providing a source of CFTR channel activity.

In another embodiment of the invention, a nucleic acid molecule capable of encoding a CFTR polypeptide comprising a secretion leader sequence may be transferred into a host cell for recombinant expression of the secreted CFTR polypeptide. Upon secretion, the CFTR polypeptide will transduce neighboring cells and/or enter the bloodstream where cells can be transduced at a distance. Secretion sequences that may be utilized are know to those of skill in the art. Such sequences include but are not limited to those of the herpes simplex VP22 protein (Elliot, 1999 Gene Therapy 6:149-51).

The present invention also provides for pharmaceutical compositions comprising an effective amount of a CFTR polypeptides, or a nucleic acid encoding such a CFTR polypeptide, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical Sciences" by E. W. Martin.

In specific embodiments, pharmaceutical compositions are administered in diseases or disorders involving an absence or decreased (relative to normal or desired) level of an endogenous CFTR protein or function, for example, in hosts where the CFTR protein is lacking, genetically defective, biologically inactive or underactive, or under expressed. Such disorders include but are not limited to cystic fibrosis.

In a specific embodiment, it may be desirable to administer the pharmaceutical compositions of the invention locally to the area in need of treatment, i.e., epithelial tissue lining the nose, lung, digestive tract and pancreas. This may be achieved by, for example, and not by way of limitation, inhalation, local infusion by injection, by means of a catheter, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers and hydrogels may be used to deliver the CFTR polypeptides of the invention.

The CFTR polypeptides will be administered in amounts which are effective to produce the desired effect in the targeted cell. Effective dosages of the CFTR polypeptides can be determined through procedures well-known to those in the art which address such parameters as biological half-life, bioavailability and toxicity. The amount of the composition of the invention which will be effective will depend on the severity of the CFTR disorder being treated, and can be determined by standard clinical techniques. Such techniques include analysis of channel activity, pulmonary function and digestive enzyme production. In addition, in vitro assays may optionally be employed to help identify optimal dosage ranges.

The present invention also provides a pharmaceutical pack or kit comprising one or more containers filled with one or more of the ingredients of the pharmaceutical compositions of the invention optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

Delivery of CFTR Polypeptide to CF Patient Airway Cells

A novel method for identification of peptides that facilitate internalization has been developed. Using this system, PTD5 is shown to deliver protein complexes and inline fusions into human airway cells and mouse lungs. Furthermore, the PTD5-ΔF508 NBD1/RD fusion protein rescued chloride channel activity as evidenced by SPQ assays. The results described below clearly demonstrate the feasibility of using PTDs to deliver proteins into airway cells, including those of the lung, and the ability of the PTDΔF508 NBD1/RD polypeptide to rescue chloride channel function.

6.1. PTD-5 Facilitates Delivery Proteins Into Differentiated Airway Cells

To determine whether the PTD5 polypeptide (RRQR-RTSKLMKR) was able to facilitate uptake into different cell types including differentiated airway epithelial cells and Calu3 cells, the ability of PTD5 to deliver avidin-β-Gal and streptavidin Cy3 to human airway cells and Calu3 cells was examined.

PTD-5 is a positively charged transduction peptide, which was biotinylated so that it can be coupled to avidin marker complexes. 150 nM of the PTD-5-avidin-β-gal complex was added to the cell culture media of various cell lines (FIG. 1). Three hours post addition of the complex, the indicated cells were fixed and stained with X-gal.

Figure 2:
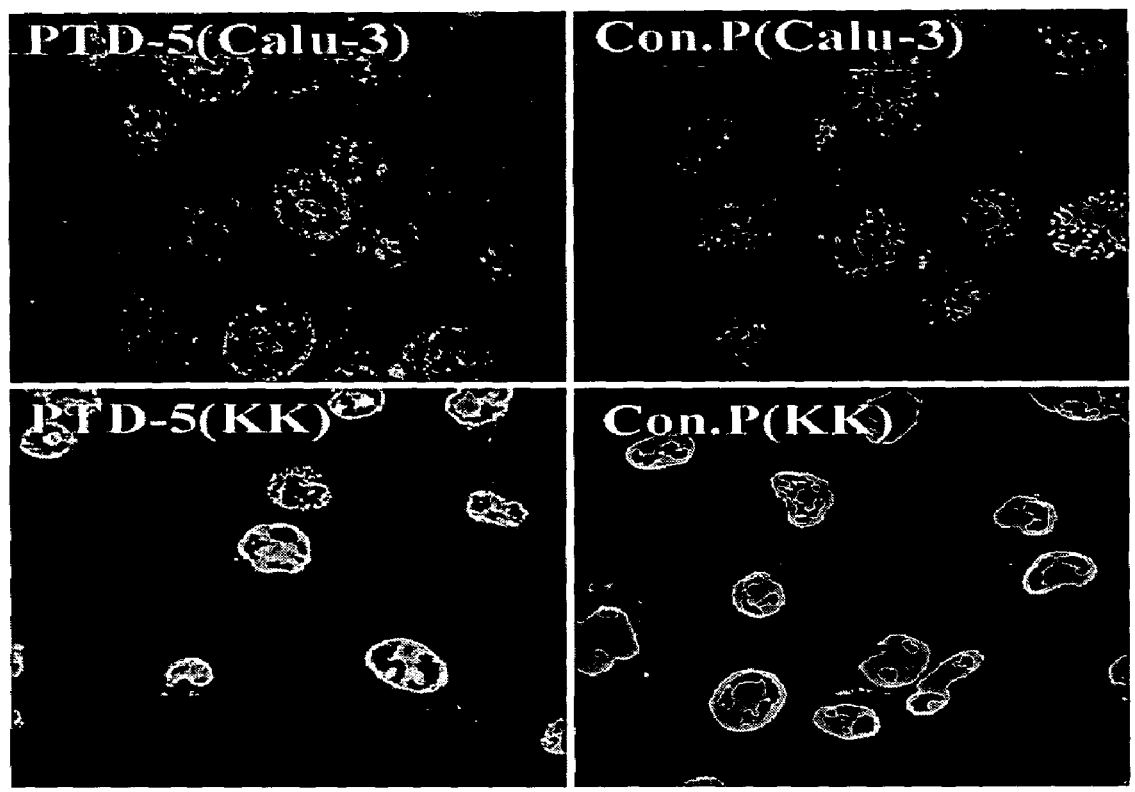
FIG. 2 shows fluorescent micrographs of Calu3 and human bronchial epthelial cells (KK) demonstrating PTD-5-facilitated protein transduction using streptavidin-Cy3.

PTD-5 was also coupled to streptavidin-Cy 3, which was added to Calu3 cell and human bronchial epthelial cells (KK) cultures at 37° C. (FIG. 2). A peptide (Con.P)-strepavdin-Cy3 was used as a control. Three hours post addition of the PTD-5-streptavidin-Cy 3, the intracellular localization of the red (Cy 3) fluorescent signals were visualized by confocal microscopy. The nuclei were counterstained using cytox green.

As shown in FIG. 1, PTD5 was able to deliver the avidin-β-gal complex to primary human airway epithelial cells (HBE144), polarized canine kidney cells (MDCK) and other cell types by microscopy. PTD-5 also delivered the streptavidin-Cy3 complex to human airway epithelial cells (KK) and Calu3 cells, as shown by confocal microscopy (FIG. 2).

6.1.2. PTD-5 Facilitates Protein Delivery Into Mouse Lung

To determine if the PTDs can facilitate protein uptake by mouse lungs, the PTD5 streptavidin-Cy3 complexes were delivered into mouse lungs intra-tracheally. The treated mice were sacrificed three hours post-delivery and tissue from the lungs was scanned by two-photon microscopy. 50 µl of 200 µM solution of the PTD-5-β-Cy3 was injected intra-tracheally into mouse lungs. Three hours post-injection, the mice were sacrificed, and the lungs were analyzed by two photon confocal microscopy for internalization. A control peptide (Con.P)-Cy3 was used as a control.

Figure 3:
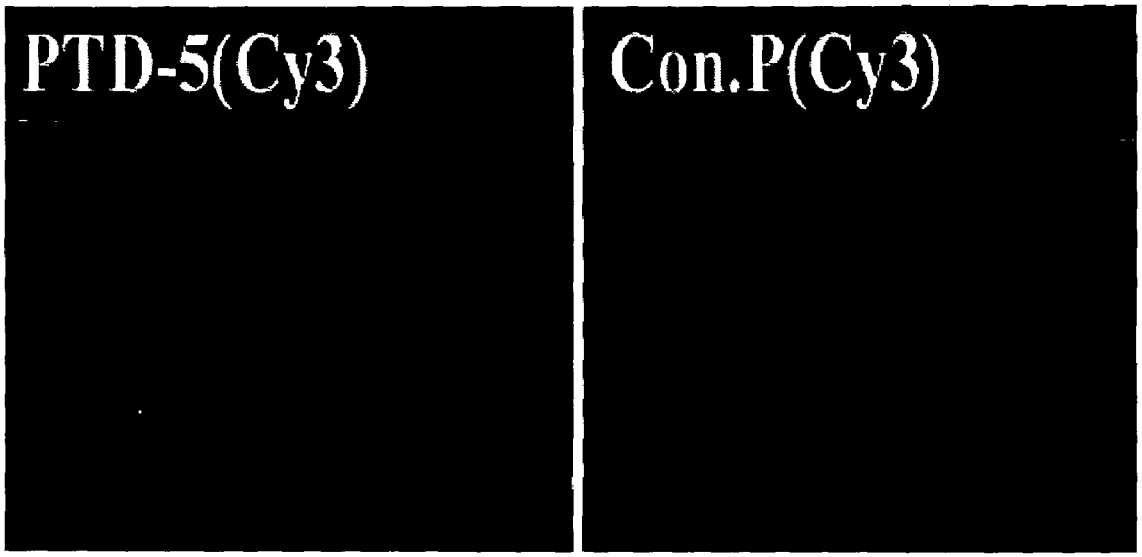
FIG. 3 shows fluorescent micrographs of PTD-5-facilitated uptake of streptavidin-Cy3 into mouse lung tissue.
Figure 4:
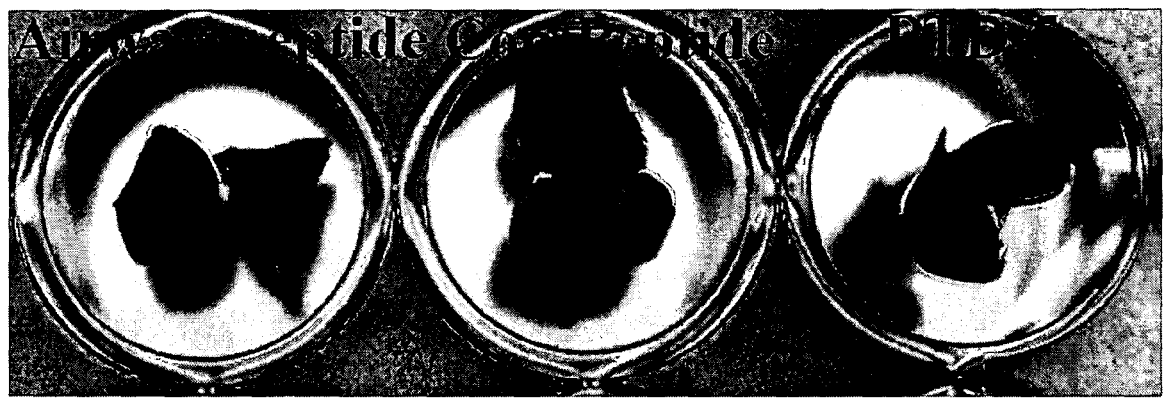
FIG. 4 shows X-gal staining of whole mouse lung tissue treated with PTD-5-streptavidin-β-gal, airway peptide and a control peptide.

As shown in FIG. 3, significant Cy3 signal was observed in the PTD-5 treated lungs, but weak signals in control peptide treated lungs. FIG. 4 shows a significant amount of staining across the whole mouse lung. Taken together, these in vitro and in vivo results suggest that the PTD5 can facilitate efficient internalization of protein into lungs thereby providing a useful method for delivery of CFTR polypeptides for pulmonary diseases including CF.

Figure 5:
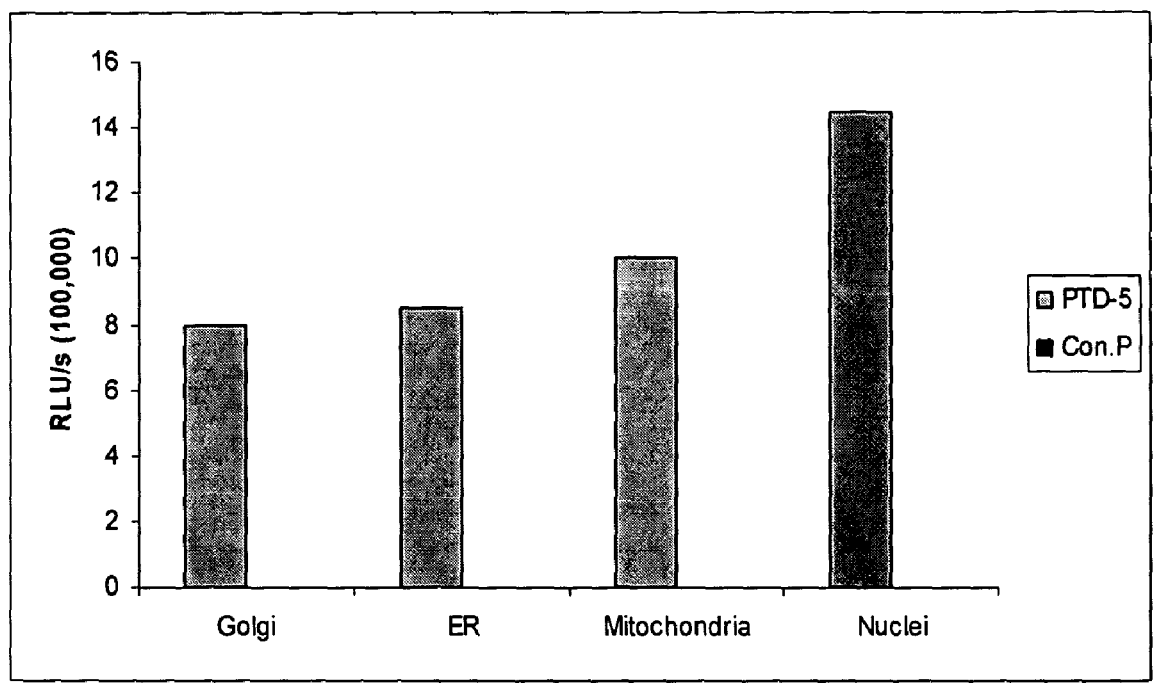
FIG. 5 is a bar graph showing the PTD-5-facilitated uptake and distribution of avidin-β-gal in various cellular organelles in human airway epithelial cells.

6.1.3. PTD-5 Facilitates Protein Delivery Into Different Organelles of Human Airway Cells To test the distribution of PTD5 facilitating uptake into human airway cells, the ability of PTD5 to deliver β-gal protein to a variety of cell organelles was examined by separation of organelles using gradient ultra-centrifugation. PTD-5-avidin-β-gal and a control peptide, (Con.P)-avidin-β-gal, were added to the media bathing the airway cell cultures and incubated at 37° C. Three hours post-addition of the complexes, the cells were washed extensively and collected for organelle isolation by gradient ultracentrifugation. The purified cell organelles were tested for β-gal activity using a Galacto-light kit (Tropix, Inc.). As shown in FIG. 5, PTD5 was able to deliver the avidin-β-gal complex to ER, Golgi, mitochondria, and nuclei after 2 hours incubation. Most notably, the fusion protein was found in the ER, which is the location necessary to facilitate release and subsequent trafficking of mutant CFTR. In contrast to PTD-5, the control peptide did not localize to any of the organelles shown in FIG. 5.

6.1.4. Construction of PTD5-eGFP and ΔF508 NBD1/RD Inline Fusions

Figure 6:
FIG. 6A is a diagram of PTD-5-eGFP and PTD-5 ΔF508NBD1-RD fusion proteins.
FIG. 6B shows the uptake of PTD-5-facilitated uptake of PTD-5-eGFP fusion peptide in Calu3 cells.
FIG. 6C shows a western blot demonstrating detection of expressed fusion peptide, PTD-5-ΔF508 NBD1-RD.
Figure 6:
Figure 6:
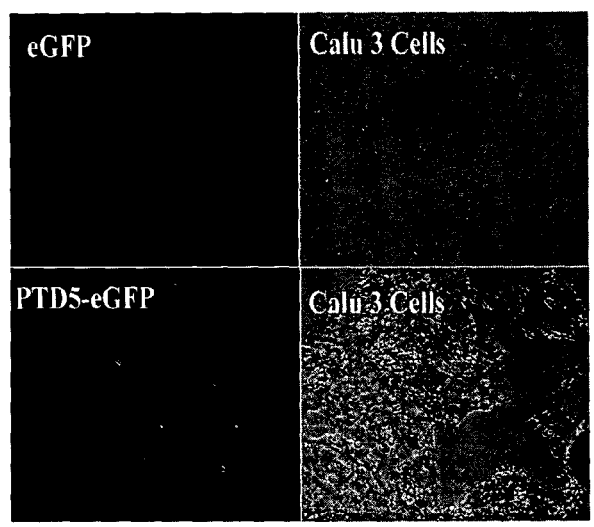
Figure 6:
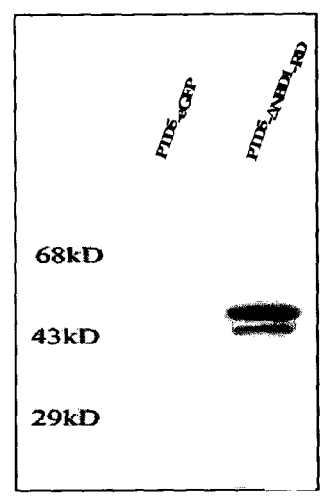

To determine if PTD5 is able to deliver proteins when fused directly to other proteins, a PTD-5 eGFP fusion protein was constructed by PCR. A chimeric eGFP protein was generated with the 12 amino acids of PTD-5 inserted at the N-terminus of the eGFP and a 6 histidine amino acid tag inserted at the C-terminus (FIG. 6A). The fusion protein was expressed in *E. coli*, purified on a nickel column and added to Calu3 cells (FIG. 6B). The fusion eGFP protein was internalized efficiently by the cells, localizing predominantly to the nuclei. The result demonstrates that PTD-5 can be used to facilitate internalization when used as a fusion protein. Given this result, the same strategy was used to construct a PTD5-ΔF 508 NBD1/RD inline fusion (FIG. 5A), and the fusion protein was expressed in *E. coli* system and purified on a nickel column. The purified fusion protein specifically reacted with an anti-CFTR RD antibody as demonstrated by western blot analysis (FIG. 6C).

6.1.5. The Function of Adenovial-ΔF508 NBD1/RD and PTD5-ΔF508 NBD1/RD Inline Fusion To test the function of adenoviral ΔF508 NBD1/RD and PTD5-ΔF508 NBD1/RD inline fusion, an SPQ assay was performed on ΔF508 mutant CF patient airway cells, using adenoviral eGFP and PTD-eGFP as controls.

Figure 7:
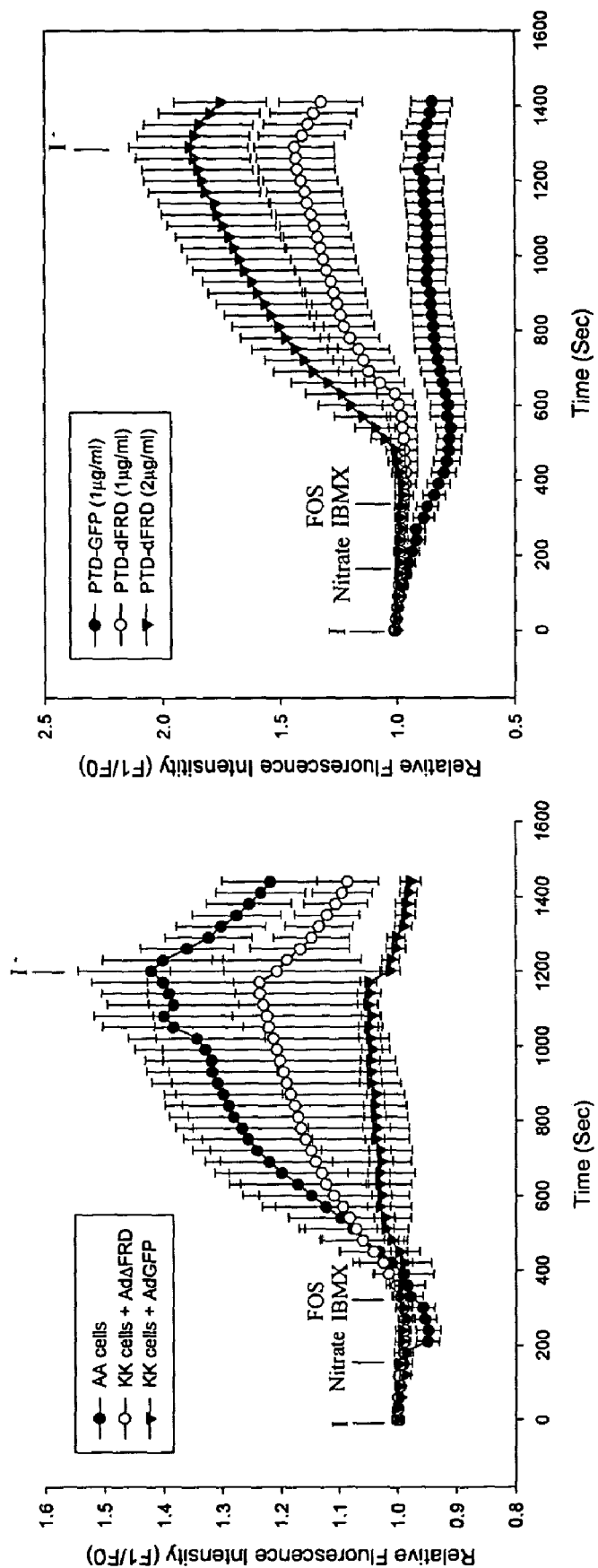
FIG. 7 shows the restoration of mutant CFTR function in human bronchial cells containing PTD-5-ΔF508 NBD1-RD using SPQ assays.

To determine if delivery of the NBD1-RD region of ΔF508 CFTR would be able to facilitate release of the trapped full length mutant CFTR protein, an adenoviral vector expressing this CFTR region and the PTD5-ΔF508NBD1-RD fusion protein were tested. To test the ability of Ad.ΔF508 NBD1-RD gene transfer and PTD5-ΔF508NBD1-RD protein transduction to restore CFTR function, SPQ assays were performed on airway epithelial cell cultures (FIG. 7). Airway cell monolayers were exposed to adenovirus or fusion proteins carrying ΔF508NBD1-RD or GFP for 3 hrs prior to Cl permeability determinations. These functional assays of Cl permeability were performed using the halide-sensitive fluorophore, SPQ (Howard et al., 1995, Am J. Physiol 269:C1565-76). Representative traces of chloride movement was determined for 10 cells in the absence and presence of 10 µM forskolin. After cellular dye loading, the cells are exposed to media containing iodide, a strong quencher of SPQ fluorescence. They are subsequently exposed to nitrate, which does not quench SPQ, and then to forskolin plus IBMX to increase intracellular cAMP levels. Dequenching of the fluorescence signal in the presence of nitrate and forskolin/IBMX is indicative of a cAMP-induced Cl permeability, a phenotype associated with wt CFTR function. Human bronchial cell lines (AA and KK) immortalized with hTERT vectors and primary human bronchial epithelial (HBE) cultures were derived from both CF and non-CF individuals.

The relative fluorescence intensity, F1/F0, was presented as a fraction of the fluorescence intensity at given time point over the average intensity of two time points after initial recording. Each trace (means +/–S.D) represents at least two-coverslip with 10 to 15 cells measured on each coverslip. The results were repeated twice.

The results showed that, in cells treated with a control adenoviral eGFP vector, no significant cAMP-stimulated halide efflux was observed, whereas 24 hours treatment with adenoviral ΔF508 NBD1-RD vector elicited a significant cAMP-dependent anion permeability (FIG. 7A). Similarly, in cells treated with a control PTD-eGFP peptide, no significant cAMP-stimulated halide efflux was observed, whereas 4 hours treatment with PTD5 ΔF508 NBD1-RD fusion elicited a significant cAMP-dependent anion permeability (FIG. 7B).

Treatment of ΔF508 cell lines with adenovirus carrying the PTD5-ΔF508NBD1-RD (FIG. 7A) or of primary cultures with the PTD5-ΔF508NBD1-RD fusion protein (FIG. 7B) caused their cAMP-dependent Cl permeabilities to recover toward normal levels.

In HBE primary cultures, the recovery of activity with the fusion peptide was dose-dependent. Control experiments performed in HeLa cells indicated that exposure to ΔFN-R in the absence of CFTR expression had no effect on Cl permeability (data not shown). These results strongly suggest that delivery of the ΔF508 CFTR NBD1 region, either by gene transfer or protein transduction, results in release of the trapped ΔF508 CFTR protein, allowing it to traffic to the cell surface where it serves as a functional channel.

6.1.6. Competitive Inhibition of Hdj2 Interaction with ΔF508CFTR BY NBD1-ΔF-RD Subdomains Hsc70 has been shown to play a key role in both the maturation and degradation of both mutant and wt CFTRs. Prolonged association of Hsc70 with CFTR promotes its degradation, probably by mediating association of CFTR with the ubiquitin ligase, CHIP. The interaction of Hsc70 with CFTR is mediated, at least in part, by the co-chaperone, Hdj2. To test whether ΔF508 CFTR ER retention is associated with the chaperone protein Hdj2, either wild type or ΔF508 mutant CFTR expression plasmids were co-transfected into 293 cells with either a eGFP or ΔF508NBD1-RD expression vectors at different plasmid molar ratios.

Figure 8:
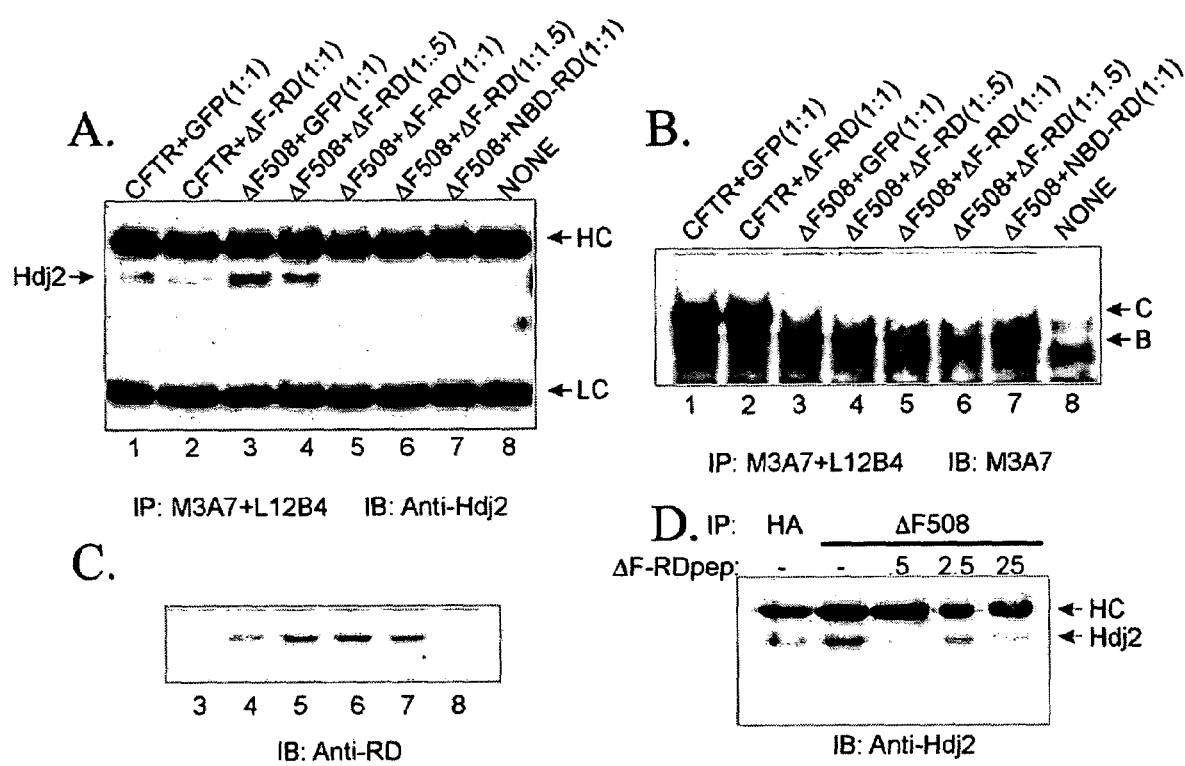
FIG. 8 shows that PTD-5-ΔF508 NBD1-RD disrupts ΔF508 CFTR interaction with chaperone Hdj2.7.

HEK293 cells were co-transfected with CFTR and GFP (lane 1), CFTR and ΔF-RD (lane 2), ΔF508 and GFP (lane 3), ΔF508 and ΔF-RD, and with different plasmid molar ratios (lanes 4, 5, and 6) and ΔF508 and NBD1-RD (lane 7) (FIGS. 8A and 8B). 48 hrs post-transfection, the cells were lysed with a lysis buffer. After pre-clearing lysates, equal amounts of lysates were used to perform immunoprecipitation (IP) using CFTR antibodies, M3A7 (1 μg) and L12B4 (1 μg) and protein A/D beads. The precipitants were washed with lysis buffer for five times. Hjd2 that co-precipitated with CFTR was fractionated in SDS-PAGE, transferred to PVDF membrane and detected by immunoblotting (IB) shown in (FIG. 8A). The same blot was used to detected CFTR expression (FIG. 8B). Densitometry was used to determine the relative affinity of Hdj2 interacting with CFTR and ΔF508 (FIG. 8C). Equal amounts of proteins were resolved in SDS-PAGE and probed with antibody against CFTR RD (FIG. 8D). The results were repeated twice.

To test whether PTD-5 ΔF508NBD1-RD could inhibit interaction of Hdj2 and ΔF508 CFTR, KK cells, a bronchial epithelial cell line carrying the ΔF508 mutation, were lysed with a lysis buffer, the lysate was treated with PTD5-NBD1-ΔF-RD and equal amount lysates were used to perform immunoprecipitation (IP) using CFTR antibodies, M3A7 (1 μg) and L12B4 (1 μg) and protein A/D beads. The precipitants were washed five times with lysis buffer. Hjd2 that co-precipitated with CFTR was fractionated by SDS-PAGE, transferred to PVDF membrane and detected by immunoblotting (IB).

These results clearly show that expression of ΔF508NBD1-RD competed for binding of Hdj2 to the full length ΔF508CFTR. Furthermore, the PTD5 ΔF508NBD1-RD fusion protein was capable of inhibiting the interaction of Hdj2 with the ΔF508 CFTR protein. These findings suggest that PTD5-ΔF508NBD1-RD fusion protein rescues mutant CFTR protein from ER degradation by competing with chaperone interactions that would otherwise lead to its degradation. They provide a mechanistic explanation for the action of PTD5-ΔF508NBD1-RD in promoting ΔF508 CFTR release from the ER.

6.1.7. Expression of ΔF508NBD1-RD Promotes Maturation of ΔF508CFTR

HEK293 cells stably transfected with CFTR, ΔF508CFTR and ΔF508CFTR with ΔF-NBD1-RD were subjected to immunofluorescence microscopy using CFTR-CT antibody. The signals were detected using a FITC-conjugated secondary antibody.

Figure 9:
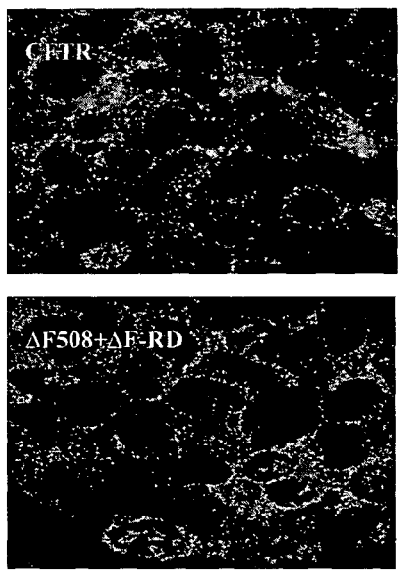
FIG. 9A shows fluorescent micrographs of HEK 293 cells stably transfected with CFTR, ΔF508CFTR and ΔF508CFTR with ΔF-NBD1-RD demonstrating that ΔF-NBD1-RD promotes maturation of ΔF508CFTR.
FIG. 9B shows an autoradigraph of immunoprecipitates from HEK293 cell lysates transfected with CFTR, ΔF508CFTR or ΔF508CFTR and ΔF-NBD1-RD demonstrating that ΔF-NBD1-RD promotes maturation of ΔF508CFTR.
Figure 9:
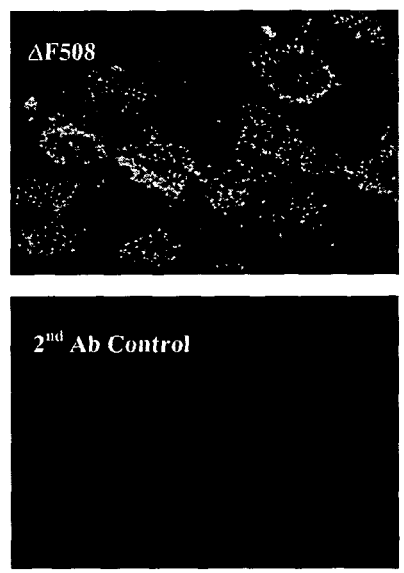
Figure 9:
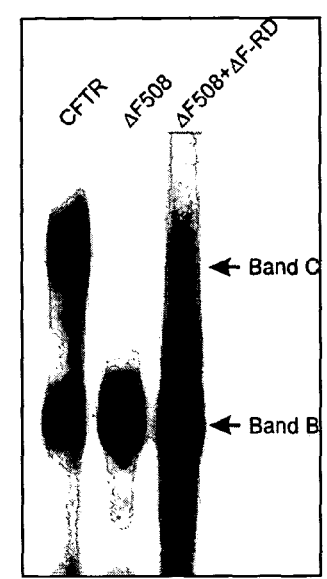

The fluorescent micrographs of HEK293 cells stably transfected with ΔF508CFTR and ΔF-NBD1-RD shows increased expression of CFTR in comparison to cells transfected only with ΔF508CFTR (FIG. 9A).

In addition, cell lysates from HEK293 cells transfected with CFTR, ΔF508CFTR or ΔF508CFTR and ΔF-NBD1-RD were immunoprecipitated with M3A7 and subjected in vitro phosphorylation in the presence of 5-unit of PKA catalytic subunit and [$\gamma$-$^{32}$P]ATP. The signals were detected by autoradiography. The autoradiograph also provides support for increased expression and promotion of mature forms of CFTR with the expression of ΔF-NBD1-RD (FIG. 9B).

7. EXAMPLE

Optimization of PTD5-ΔF508 NBD1/RD Fusion Protein

Protein therapy approaches for treating cystic fibrosis have encountered problems with protein instability and/or immunogenecity. In order to overcome such problems, the experiments described below teach mapping of ΔF 508 NBD1-RD for small functional peptides that are able to inhibit ΔF508 CFTR ER retention associated with cytoplasmic chaperones. SPQ assay screens are utilized to identify truncated protein or peptides that are able to restore chloride channel function. Those truncated protein or peptides that are shown to be functional using SPQ may also be reassessed using patch-clamp analysis on ΔF508 homozygous CF patient airway cells.

7.1. Construction of PTD5 Truncated NBD1-RDfusion Protein

Construction of a PTD5 truncated NBD1-RD fusion protein is performed by PCR. The twelve amino acids of PTD-5 is inserted at the amino terminus of the truncated NBD1-RD in which a 6 histidine amino acid tag has been inserted at the C-terminus. The fusion protein is expressed in the pET3B plasmid in E. coli, followed by purification on a Nickel column. Truncated peptides may be synthesized by Fmoc (N-(9-fluorenyl)methoxycarbonyl) solid phase synthesis, N-terminally biotinylated, purified by reversed-phase high performance liquid chromatography to >90% purity on an acetonitrile/H₂O-trifluoroacetic acid gradient, and confirmed by electrospray ionization mass spectrometry (Peptide Synthesis Facility, University of Pittsburgh).

7.2. SPQ Method for Screening the Truncated Protein Function

To test the function of PTD5-ΔF508 NBD1/RD truncated inline fusions, an SPQ assay is performed on ΔF508 mutant CF patient airway cells. Representative traces of chloride movement is measured for 10 cells in the absence and presence of 10 µM forskolin. The cells are seeded to glass coverslips, cultured for 2 days, followed by addition of PTD5 fusion proteins for 4 hrs. The cells are then loaded with SPQ fluorescent dye by hypotonic loading as described previously. Briefly, cells are incubated at room temperature for 4 min with a 1:1 mixture of Cl buffer (126 mM NaCl, 5 mM KCl, 1.5 mM CaCl, 1.0 mM MgCl, 20 mM Hepes, 0.1% bovine serum albumin, 0.1% D-glucose, pH 7.2) and distilled $H_2O_2$ containing 5 mM SPQ. The glass coverslip is mounted in a chamber on a stage heated to 37° C., which is arranged for continuous flow of warmed buffer solutions and studied one-by-one using an upright Zeiss epifluorescence microscope. Fluorescence is excited at 355 nm (Omega Optical Inc., Brattleboro, Vt.) by a 75-watt xenon lamp. Excitation light is reflected by a 400-nm fused silica dichroic mirror (Omega Optical Inc.) and illuminated the cells through a 20× objective (numerical aperature of 0.75, working distance of 0.66 mm; Nikon Inc., Garden City, N.Y.). Emitted light is filtered by a 450-nm lens and detected by a microchannel plate image intensifier (Model KS-1381) in series with a CCD-200 solid-state video camera (Video Scope International, Ltd., Washington, D.C.). The images are quantified with a Model MVP-AT frame grabber board (Matrox, Quebec, Canada) mounted internally in a host 386 computer and processed with Image-1 F1 software (Universal Imaging Corp., West Chester, Pa.). Every image taken (0.26 s) represents the average of 16 images. Successive images are recorded at a rate of 1 every 5 s. The "blank field" obtained by closing the camera shutter is used as background image and subtracted prior to acquisition of the images. SPQ fluorescence will be calibrated by measuring the fluorescence in the absence of chloride (maximum fluorescence) and in the presence of a solution that quenches all the SPQ fluorescence (150 mM KSCN, 10 µM valinomycin). Photobleaching is corrected for by subtracting a straight line that connects the two points at the beginning of the experiment and before KSCN+valinomycin application. Results are expressed as rates (relative fluorescence units/minute). The rates are calculated by fitting a single exponential equation to the initial portion of each single curve after correction for photobleaching.

7.3. Whole Cell Patch-clamp to Verify Channel Activity of the Screened Protein As described above, the SPQ method can be utilized to test Cl channel function. To increase the specificity of the method, a whole cell patch clamp method can be utilized to verify the SPQ data using PTD-5 ΔF508 NBD1/RD. Briefly, cells at 50% confluence are treated with PTD fusion peptide or adenovirus carrying ΔF508 NBD1/RD for four hours and subjected to whole cell patch clamp by standard methods. Currents are recorded at −60 mV and current-voltage relations are obtained before and after the cells are stimulated with 5-10 µM forskolin; all procedures are performed at 37° C. The bath solution contained (in mM) 150 NaCl, 2 MgCl₂, 1 EGTA, 5 HEPES and 0.5 CaCl₂ (pH=7.3). The pipette solution contains (in mM) 150 NaCl, 2 MgCl₂, 5 HEPES and 2 CaCl₂ (pH=7.3). Data is amplified using an Axopatch 200A patch-clamp amplifier and recorded to disk by a Digidata A/D interface for later analysis with pCLAMP8. The data is low-pass filtered and digitized at 1 kHz. Primary human airway (HBE) cells treated with fusion peptide or recombinant virus show forskolin-stimulated currents typical of those associated with CFTR. The current-voltage relations were linear and the stimulation of current reversible. These findings indicate that the characteristic CFTR conductance in cells endogenously expressing ΔF508 CFTR can be restored by this treatment.

8. EXAMPLE

Optimization of Protein Uptake and Differentiated Human Airway Epithelial Cells The treatment of CF has been hindered due to the poor internalization, or transduction, of genes or proteins into polarized airway cells. PTDs are generally short peptides enriched in positively charged amino acids able to facilitate uptake proteins into live cells. Mutagenesis and sequence screens have subsequently revealed additional naturally occurring and synthetic peptide sequences that can function as PTDs when coupled to small fluorophores or large proteins. Recently published reports suggest that the different PTD sequences have different efficacies for transduction of different cell types. These findings have led to increased focus on strategies to select an optimal PTD to yield high transduction efficiency for certain type of cells. As demonstrated herein, PTD5 can efficiently transduce airway cells. The following Table contains a list of PTD candidates for transduction screens on polarized airway cells.

TABLE I

| SEQUENCES OF THE PROTEIN TRANSDUCTION DOMAINS | | | |
|---|---|---|---|
| PTD | Length | Sequence | SEQ ID NO |
| PTD-4 | 12 | PIRRRKKLRRLK | 1 |
| PTD-5 | 12 | RRQRRTSKLMKR | 2 |
| TAT | 11 | YGRKKRRQRRR | 3 |
| Ant | 16 | RQIKIWFQNRRMKWKK | 4 |
| 4R | 4 | RRRR | 5 |
| 6R | 6 | RRRRRR | 6 |
| 8R | 8 | RRRRRRRR | 7 |
| 10R | 10 | RRRRRRRRRR | 8 |
| 12R | 12 | RRRRRRRRRRRR | 9 |
| 4K | 4 | KKKK | 10 |
| 6K | 6 | KKKKKK | 11 |
| 8K | 8 | KKKKKKKK | 12 |
| 10K | 10 | KKKKKKKKKK | 13 |
| 12K | 12 | KKKKKKKKKKKK | 14 |
| 5RQ | 5 | RRQRR | 15 |
| 8RQ | 8 | RRQRRQRR | 16 |
| 11RQ | 11 | RRQRRQRRQRR | 17 |
| Con P | 12 | ARPLEHGSDKAT | 18 |
| AWP-1 | 12 | TLPSPLALLTVH | 19 |
| ACP-1 | 12 | DPATNPGPHFPR | 20 |

Figure 10:
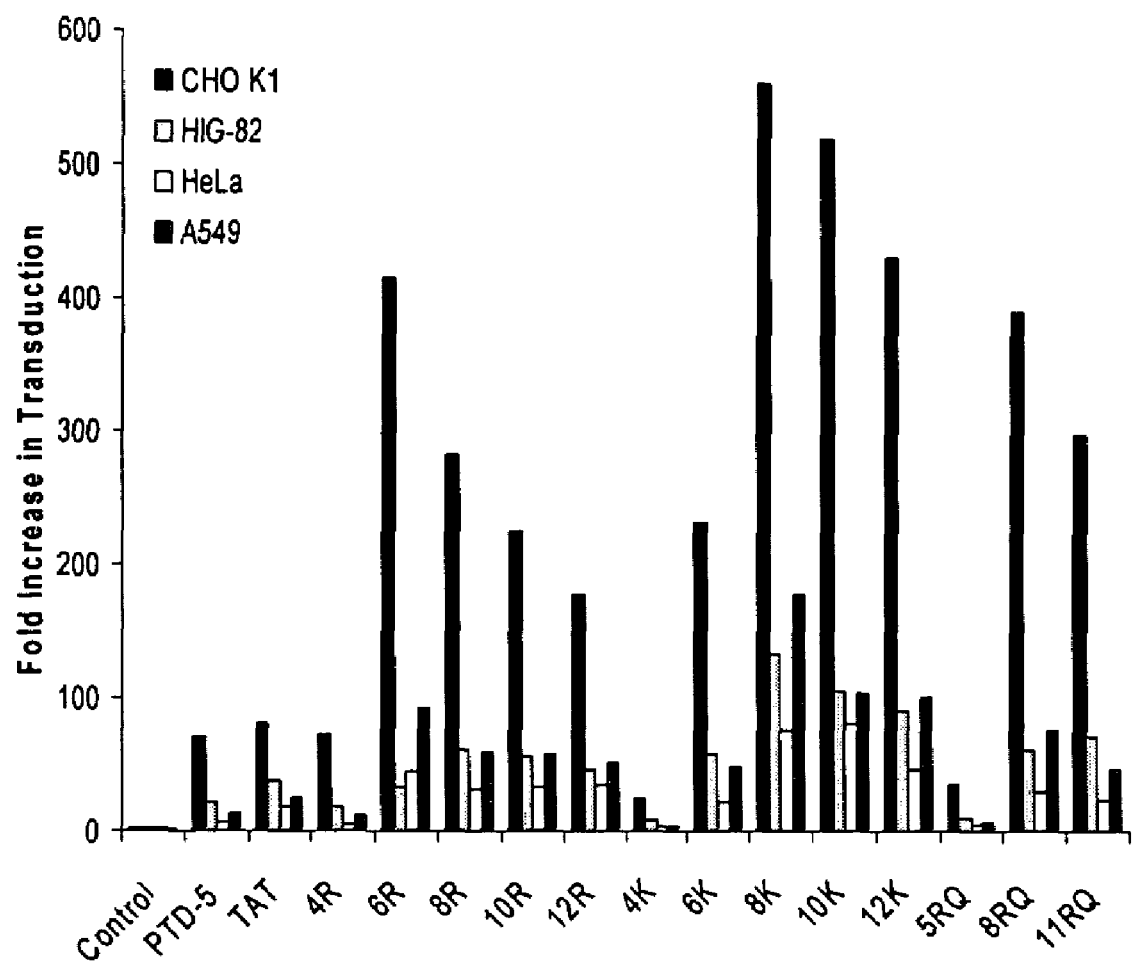
FIG. 10 is a bar graph of the efficiency of transduction of various internalizing peptides in HeLa, A549, Cho and Hig-82 cell lines.

The listed transduction peptides in Table 1 may also have varying abilities to deliver different marker complexes into a wide variety of cells. Different peptides were biotinylated and coupled to different streptavidin complexes such as β-gal, Cy3 or Alexa Flour 488. The panel of peptides were tested in four different cell lines, HeLa, A549, CHO and Hig-82 (a rabbit synovial cell line) by conjugating the peptides to steptavidin-Alexa Flour 488. The transduction was quantitated by FACS following trypsinization of the cells. As shown in FIG. 10, the 6 and 8 arginine and 8 and 10 lysine peptides were the most efficient for transduction of the four different cell types. In addition, these peptides were more effective than the Tat derived PTD or PTD-5. These peptides may be as effective as PTD-5 for functional delivery of NBD1.

Odd numbered iterations of polylysine peptides and polyarginine peptides wherein the peptide may comprise 5 to 19 multiple residues may be used as internalizing peptides.

8.1. Peptide Synthesis and Quantitation

The peptides listed in Table I are synthesized by Fmoc (N-(9-fluorenyl)methoxycarbonyl) solid phase synthesis, N-terminally biotinylated, purified by reversed-phase high performance liquid chromatography to >90% purity on an acetonitrile/H2O-trifluoroacetic acid gradient, and confirmed by electrospray ionization mass spectrometry (Peptide Synthesis Facility, University of Pittsburgh). Lyophilized peptides are reconstituted in distilled water to 2 mM stock concentrations. Peptide solutions containing primary amines (PTD-5, TAT, and lysine homopolymers) are quantitated by ninhydrin chemistry using L-norleucine (Sigma) as a standard. Arginine-rich peptides (arginine homopolymers and RQ series peptides; Table I) are quantitated by total amino acid hydrolysis, using L-norleucine, glutamine (hydrolyzed to glutamic acid), and hydrolyzed biotin as internal controls.

8.2. Cell Cultures

Human ΔF508 homozygous CF patient airway epithelial cells are isolated from lung transplantation and cultured in 50% Ham's F-12 and 50% DMEM medium at 37° C. in 5% CO2. AA and KK cell lines are cultured in 50% Ham's F-12 and 50% DMEM medium at 37° C. in 5% CO2. AA and KK cell lines.

8.3. Enzymatic Quantitation of Protein Transduction

PTD-β-galactosidase complexes are formed by preincubating streptavidin-β-galactosidase (Sigma Chemical Co.) with a 30-fold excess of biotinylated peptides for 2 hr at room temperature. Complexes are added to serum-containing medium (10% fetal calf serum) in each well of 24-well plates with confluent cell monolayers of human ΔF508 homozygous CF patient airway epithelial cells, at 20 nM streptavidin concentrations and incubated for 3 hr at 37° C. The treated cells are washed six times in TBS, and soluble extracts are obtained by incubating cells in 0.2% Triton X-100 lysis buffer, followed by pelleting insoluble debris at 14,000 rpm. β-Galactosidase recovered from the cellular extracts is quantitated by 1,2-dioxetane-based light emission (Tropix, Inc.). Fluorescence is measured in a Berthold AutoLumat luminometer, and relative light units are normalized to protein content as measured by Bradford protein assay (Bio-Rad) using bovine serum albumin as a standard. Each condition tested is performed in triplicate, with means and S.D. values calculated.

8.4 Flow Cytometric Quantitation of Protein Transduction

PTD-streptavidin-fluorophore complexes are formed by pre-incubating 1.7 µM streptavidin-Alexa Fluor 488 (SA-488; Molecular Probes, Inc., Eugene, Oreg.) with 1 mM biotinylated peptides for 30 min at room temperature. A single human ΔF508 homozygous CF patient airway epithelial cell suspension is generated by incubating confluent adherent cells in Hanks' solution-based enzyme-free cell dissociation buffer (Invitrogen). The treated cells are pelleted, counted, and resuspended at a final concentration of $2\times10^6$ cells/ml in serum-containing media (10% fetal calf serum). PTD-streptavidin complexes are then added to a final concentration of 20 nM streptavidin, and cells are incubated at 37° C. for 1 hr. The cells are washed twice in phosphate-buffered saline, trypsinized for 20 min at 37° C., washed again, and resuspended at $2\times10^6$ cells/ml in phosphate-buffered saline. Trypsinization is used to eliminate non-internalized, surface-bound complexes. 7-Aminoactinomycin D (7-AAD; BD Pharmingen) is added to a final concentration of 0.5 ng/µl 10 min prior to analysis by flow cytometry for dead cell exclusion. The treated cells are gated on the 7-AAD-negative cell populations, measuring fluorescence excited by a 488-nm argon ion laser line in a Becton Dickinson FACSCalibur flow cytometer, with 10,000 events collected from the gated population. Flow cytometry data is analyzed with CellQuest (Becton Dickinson).

The optimal PTD identified in the screen of primary human airway epithelial cells will be further characterized. In particular, experiments are performed to determine the efficiency of internalization, cellular localization, and cell toxicity. Optimal PTDs can be used, together with the selected truncated NBD1-RD peptides to construct an optimal PTD mediated protein or peptide therapeutic for CF treatment.

Once an optimal PTD and truncated NBD1-RD polypeptide has been identified, the newly formed PTD fusion is assayed for restoration of CFTR function on CFTR)F508 homozygous CF patient airway epithelial cells using the SPQ assay and patch-clamp methods described herein.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

We claim:

1. An isolated polypeptide comprising:
(a) an internalizing peptide; and
(b) the Nucleotide Binding Domain 1 of the human Cystic Fibrosis Trans-membrane conductance Regulator protein, wherein the amino acid at position 508 numbered relative to the entire human Cystic Fibrosis Trans-membrane conductance Regulator protein is deleted, and wherein the polypeptide enhances Cystic Fibrosis Trans-membrane conductance Regulator channel activity when present in a cell expressing a mutant Cystic Fibrosis Trans-membrane conductance Regulator channel.

2. The polypeptide of claim 1, wherein the polypeptide further comprises the Regulatory domain of the Cystic Fibrosis Trans-membrane conductance Regulator protein.

3. The polypeptide of claim 1 wherein the internalizing peptide is selected from the group consisting of SEQ ID NOS:1-19 and SEQ. ID. NO. 20.

4. The polypeptide of claim 1 wherein the internalizing peptide is SEQ ID NO:2.

5. The polypeptide of any one of claims 1, 2, 3 or 4, wherein the polypeptide further comprises a secretion leader sequence.

* * * * *

SEQUENCE LISTING

<160> NUMBER OF SEQ ID NOS: 20

<210> SEQ ID NO 1
<211> LENGTH: 12

```
<212> TYPE: PRT
<213> ORGANISM: Artificial Sequence
<220> FEATURE:
<223> OTHER INFORMATION: PTD-4

<400> SEQUENCE: 1

Pro Ile Arg Arg Arg Lys Lys Leu Arg Arg Leu Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: PTD-5

<400> SEQUENCE: 2

Arg Arg Gln Arg Arg Thr Ser Lys Leu Met Lys Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: TAT

<400> SEQUENCE: 3

Tyr Gly Arg Lys Lys Arg Arg Gln Arg Arg
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Ant

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 4
<212> TYPE: PRT
<213> ORGANISM: Artificial Sequence
<220> FEATURE:
<223> OTHER INFORMATION: 4R

<400> SEQUENCE: 5

Arg Arg Arg Arg
1

<210> SEQ ID NO 6
<211> LENGTH: 6
<212> TYPE: PRT
<213> ORGANISM: Artificial Sequence
<220> FEATURE:
<223> OTHER INFORMATION: 6R

<400> SEQUENCE: 6

Arg Arg Arg Arg Arg Arg
1               5

<210> SEQ ID NO 7
<211> LENGTH: 8
<212> TYPE: PRT
```

```
<213> ORGANISM: Artificial Sequence
<220> FEATURE:
<223> OTHER INFORMATION: 8R

<400> SEQUENCE: 7

Arg Arg Arg Arg Arg Arg Arg Arg
 1               5

<210> SEQ ID NO 8
<211> LENGTH: 10
<212> TYPE: PRT
<213> ORGANISM: Artificial Sequence
<220> FEATURE:
<223> OTHER INFORMATION: 10R

<400> SEQUENCE: 8

Arg Arg Arg Arg Arg Arg Arg Arg Arg Arg
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: 12R

<400> SEQUENCE: 9

Arg Arg Arg Arg Arg Arg Arg Arg Arg Arg Arg Arg
 1               5                  10

<210> SEQ ID NO 10
<211> LENGTH: 4
<212> TYPE: PRT
<213> ORGANISM: Artificial Sequence
<220> FEATURE:
<223> OTHER INFORMATION: 4K

<400> SEQUENCE: 10

Lys Lys Lys Lys
 1

<210> SEQ ID NO 11
<211> LENGTH: 6
<212> TYPE: PRT
<213> ORGANISM: Artificial Sequence
<220> FEATURE:
<223> OTHER INFORMATION: 6K

<400> SEQUENCE: 11

Lys Lys Lys Lys Lys Lys
 1               5

<210> SEQ ID NO 12
<211> LENGTH: 8
<212> TYPE: PRT
<213> ORGANISM: Artificial Sequence
<220> FEATURE:
<223> OTHER INFORMATION: 8K

<400> SEQUENCE: 12

Lys Lys Lys Lys Lys Lys Lys Lys
 1               5

<210> SEQ ID NO 13
<211> LENGTH: 10
<212> TYPE: PRT
<213> ORGANISM: Artificial Sequence
```

-continued

```
<220> FEATURE:
<223> OTHER INFORMATION: 10K

<400> SEQUENCE: 13

Lys Lys Lys Lys Lys Lys Lys Lys Lys Lys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: 12K

<400> SEQUENCE: 14

Lys Lys Lys Lys Lys Lys Lys Lys Lys Lys Lys Lys
1               5                   10

<210> SEQ ID NO 15
<211> LENGTH: 5
<212> TYPE: PRT
<213> ORGANISM: Artificial Sequence
<220> FEATURE:
<223> OTHER INFORMATION: 5RQ

<400> SEQUENCE: 15

Arg Arg Gln Arg Arg
1               5

<210> SEQ ID NO 16
<211> LENGTH: 8
<212> TYPE: PRT
<213> ORGANISM: Artificial Sequence
<220> FEATURE:
<223> OTHER INFORMATION: 8RQ

<400> SEQUENCE: 16

Arg Arg Gln Arg Arg Gln Arg Arg
1               5

<210> SEQ ID NO 17
<211> LENGTH: 11
<212> TYPE: PRT
<213> ORGANISM: Artificial Sequence
<220> FEATURE:
<223> OTHER INFORMATION: 11RQ

<400> SEQUENCE: 17

Arg Arg Gln Arg Arg Gln Arg Arg Gln Arg Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: control, Con P

<400> SEQUENCE: 18

Ala Arg Pro Leu Glu His Gly Ser Asp Lys Ala Thr
1               5                   10

<210> SEQ ID NO 19
<211> LENGTH: 12
<212> TYPE: PRT
<213> ORGANISM: Artificial Sequence
<220> FEATURE:
```

```
<223> OTHER INFORMATION: AWP-1

<400> SEQUENCE: 19

Thr Leu Pro Ser Pro Leu Ala Leu Leu Thr Val His
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: ACP-1

<400> SEQUENCE: 20

Asp Pro Ala Thr Asn Pro Gly Pro His Phe Pro Arg
 1               5                  10
```